United States Patent [19]

Müller et al.

[11] Patent Number: 5,356,865
[45] Date of Patent: Oct. 18, 1994

[54] SUBSTITUTED 5-ALKOXY-1,2,4-TRIAZOL-3-(THI)ONES

[75] Inventors: Klaus-Helmut Müller, Duesseldorf; Klaus König, Odenthal; Joachim Kluth, Langenfeld; Klaus Lürssen, Bergisch Gladbach; Hans-Joachim Santel, Leverkusen; Robert R. Schmidt, Bergish Gladbach, all of Fed. Rep. of Germany

[73] Assignee: Bayer Aktiengesellschaft, Leverkusen, Fed. Rep. of Germany

[21] Appl. No.: 976,185

[22] Filed: Nov. 6, 1992

Related U.S. Application Data

[63] Continuation-in-part of Ser. No. 757,785, Sep. 11, 1991, abandoned.

Foreign Application Priority Data

Sep. 22, 1990 [DE] Fed. Rep. of Germany ....... 4030063

[51] Int. Cl.$^5$ .................. A01N 43/653; C07D 249/12
[52] U.S. Cl. .................... 504/273; 548/263.4
[58] Field of Search ...................... 548/263.4; 504/273

[56] References Cited

U.S. PATENT DOCUMENTS

| | | | |
|---|---|---|---|
| 4,948,417 | 8/1990 | Lindig et al. | 548/263.2 |
| 5,061,311 | 10/1991 | Findeisen et al. | 548/263.2 |

FOREIGN PATENT DOCUMENTS 0267491  5/1988  European Pat. Off. .

OTHER PUBLICATIONS

Chemical Abstracts, vol. 68, Feb. 12, 1968, No. 7. 68:29639e.
Chemical Abstracts, vol. 89, Jul. 17, 1978, No. 3. 89:24226e.
Chemical Abstracts, vol. 101, Aug. 27, 1984, No. 9. 71922s.

*Primary Examiner*—Patricia L. Morris
*Attorney, Agent, or Firm*—Sprung Horn Kramer & Woods

[57] ABSTRACT

Herbicidal 5-alkoxy-1,2,4-triazol-3-(thi)ones of the gerneral formula

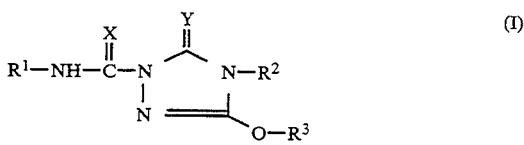
(I)

(in which the radicals $R^1$, $R^2$, $R^3$, X and Y have the meanings given in the description), processes for their preparation, and their use as herbicides, and also new intermediates of the formula (II)

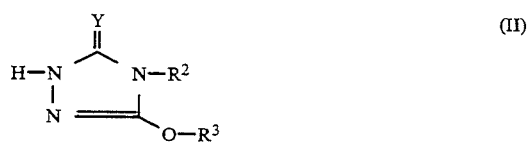

(II)

7 Claims, No Drawings

SUBSTITUTED 5-ALKOXY-1,2,4-TRIAZOL-3-(THI)ONES

This is a continuation-in-part of application Ser. No. 757,785, filed Sep. 11, 1991, now abandoned.

The invention relates to new substituted 5-alkoxy-1,2,4-triazol-3-(thi)ones, a plurality of several processes, and also new intermediates for their preparation, and their use as herbicides.

It has been disclosed that certain substituted triazolones such as, for example, 4-amino-5-methyl-2-phenylaminocarbonyl-2,4-dihydro-3H-1,2,4-triazol-3-one, have herbicidal properties (cf. EP-A 283,876, EP-A 294,666, EP-A 298,371). However, the herbicidal activity of these compounds is not entirely satisfactory in all fields of application.

New substituted 5-alkoxy-1,2,4-triazol-3-(thi)ones of the general formula ( I )

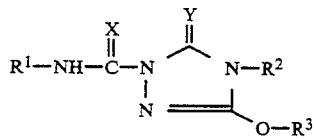

in which
R$^1$ represents alkyl, alkenyl, alkinyl, halogenoalkyl, halogenoalkenyl, halogenoalkinyl, cyanoalkyl, hydroxyalkyl, alkoxyalkyl, alkoximinoalkyl, alkoxycarbonylalkyl, alkoxycarbonylalkenyl, alkylaminoalkyl or dialkylaminoalkyl, or represents in each case optionally substituted cycloalkyl, cycloalkylalkyl, cycloalkenyl or cycloalkenylalkyl, or represents optionally substituted heterocyclylalkyl, or represents alkoxy, alkenyloxy or alkinyloxy, or represents in each case optionally substituted aralkyl, aryloxyalkyl, aralalkenyl, arylalkinyl, aroyl, aryl, aralkyloxy or aryloxy.
R$^2$ represents alkyl, alkenyl, alkinyl, halogenoalkyl, halogenoalkenyl, halogenoalkinyl, alkoxyalkyl, cyanoalkyl, alkoxy, cycloalkyl or cycloalkylalkyl,
R$^3$ represents alkyl, alkenyl, alkinyl, halogenoalkyl, halogenoalkenyl, halogenoalkinyl, alkoxyalkyl or cyanoalkyl,
X represents oxygen or sulphur and
Y represents oxygen or sulphur,
have now been found.

Furthermore, it has been found that the new substituted 5-alkoxy-1,2,4-triazol-3-(thi)ones of the general formula (I) are obtained when
(a) 5-alkoxy-1,2,4-triazol-3-(thi)ones of the general formula (II)

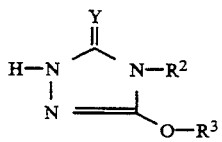

in which
R$^2$, R$^3$ and Y have the abovementioned meaning, are reacted with iso(thio)cyanates of the general formula (III )

in which
R$^1$ and X have the abovementioned meanings, if appropriate in the presence of a diluent and if appropriate in the presence of a basic reaction auxiliary, or when
(b) 5-alkoxy-1,2,4-triazol-3-(thi)ones of the general formula (II)

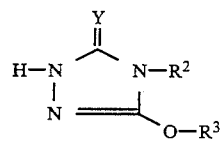

in which
R$^2$, R$^3$ and Y have the abovementioned meaning are reacted with reactive (thio-)carbamates of the general formula (IV)

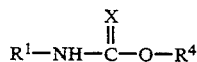

in which
R$^1$ and X have the abovementioned meanings and
R$^4$ represents alkyl, aralkyl or aryl,
if appropriate in the presence of a diluent and if appropriate in the presence of a basic reaction auxiliary, or when
(c) 5-alkoxy-1,2,4-triazol-3-(thi)one derivatives of the general formula (V)

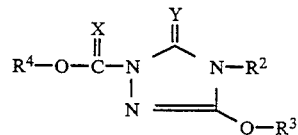

in which
R$^2$, R$^3$, X and Y have the abovementioned meanings and
R$^4$ represents alkyl, aralkyl or aryl,
are reacted with amino compounds of the general formula (VI)

in which
R$^1$ has the abovementioned meaning,
if appropriate in the presence of a diluent and if appropriate in the presence of a basic reaction auxiliary.

Finally, it has been found that the new substituted 5-alkoxy-1,2,4-triazol-3-(thi)ones of the general formula (I) are distinguished by powerful herbicidal activity.

Surprisingly, the new compounds of the formula (I) show a considerably better herbicidal activity than the compound 4-amino-5-methyl-2-phenylaminocarbonyl-2,4-dihydro-3H-1,2,4-triazol-3-one, which is known.

Formula (I) provides a general definition of the substituted 5-alkoxy-1,2,4-triazol-3-(thi)ones according to the invention. Preferred compounds of the formula (I) are those in which
R$^1$ represents in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, each of which has 2 to 8 carbon atoms and 1 to 15 or 13 identical or different halogen atoms, cyanoalkyl having 1 to 8 carbon atoms, hydroxyalkyl having 1 to 8 carbon atoms and 1 to 6 hydroxyl groups, alkoxyalkyl, alkoximinoalkyl, alkoxycarbonylalkyl or alkoxycarbonylalkenyl, each of which has up to 6 carbon atoms in the individual alkyl or alkenyl moieties, alkylaminoalkyl or dialkylaminoalkyl, each of which has 1 to 6 carbon atoms in the individual alkyl moieties, or represents cycloalkyl, cycloalkylalkyl, cycloalkenyl or cycloalkenylalkyl, each of which has 3 to 8 carbon atoms in the cycloalkyl or cycloalkenyl moiety and if appropriate 1 to 6 carbon atoms in the alkyl moiety and each of which is optionally monosubstituted or polysubstituted by identical or different substituents, the following being selected as preferred substituents in the cyclic and optionally in the aliphatic moiety: halogen, cyano, and in each case straight-chain or branched alkyl or halogenoalkyl, each of which has 1 to 4 carbon atoms and if appropriate 1 to 9 identical or different halogen atoms, or in each case divalent alkanediyl or alkenediyl, each of which has up to 4 carbon atoms; $R^1$ furthermore represents heterocyclylalkyl which has 1 to 6 carbon atoms in the straight-chain or branched alkyl moiety and 1 to 9 carbon atoms as well as 1 to 3 hetero atoms—in particular nitrogen, oxygen and/or sulphur—in the heterocyclyl moiety and each of which is optionally monosubstituted or polysubstituted by identical or different substituents, the following being selected as preferred substituents: halogen, cyano, nitro, and in each case straight-chain or branched alkyl, alkoxy, alkylthio, halogenoalkyl, halogenoalkoxy, halogenoalkylthio or alkoxycarbonyl, each of which has 1 to 5 carbon atoms and if appropriate 1 to 9 identical or different halogen atoms; $R^1$ furthermore represents in each case straight-chain or branched alkoxy having 1 to 8 carbon atoms, alkenyloxy having 2 to 8 carbon atoms or alkinyloxy having 2 to 8 carbon atoms, and finally represents aralkyl, aryloxyalkyl, arylalkenyl, arylakinyl, aralkyloxy, aryloxy, aroyl or aryl, each of which has 6 or 10 carbon atoms in the aryl moiety and if appropriate up to 8 carbon atoms in the alkyl, alkenyl or alkinyl moiety, and each of which is optionally monosubstituted or polysubstituted by identical or different substituents, suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each of which has 1 to 6 carbon atoms and if appropriate 1 to 9 identical or different halogen atoms, cycloalkyl having 3 to 6 carbon atoms and phenoxy, and suitable optional alkyl substituents being: halogen or cyano, $R^2$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl or alkoxy, each of which has 1 to 6 carbon atoms in the individual alkyl moieties, cyanoalkyl having 1 to 8 carbon atoms, or represents cycloalkylalkyl or cycloalkyl, each of which has 3 to 7 carbon atoms in the cycloalkyl moiety and if appropriate 1 to 6 carbon atoms in the straight-chain or branched alkyl moiety, $R^3$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl having 1 to 6 carbon atoms in each of the individual alkyl moieties, or represents cyanoalkyl having 1 to 8 carbon atoms, X represents oxygen or sulphur and Y represents oxygen or sulphur and halogen in the substitution patterns mentioned in the case of $R^1$, $R^2$ and $R^3$ represents fluorine, chlorine, bromine and iodine.

Particularly preferred compounds of the formula (I) are those in which $R^1$ represents methyl, ethyl, n- or i-propyl, n-, i-, s- or t-butyl, in each case straight-chain or branched pentyl, hexyl, heptyl, octyl, nonyl, decyl or dodecyl, or represents allyl, propenyl, n- or i-butenyl, n- or i-pentenyl, n- or i-hexenyl, propargyl, n- or i-butinyl, n- or i-pentinyl, n- or i-hexinyl, or represents straight-chain or branched halogenoalkyl having 1 to 4 carbon atoms and 1 to 9 identical or different halogen atoms, in particular fluorine, chlorine or bromine, or represents in each case straight-chain or branched halogenoalkenyl or halogenoalkinyl, each of which has 3 to 5 carbon atoms and 1 to 3 halogen atoms, in particular fluorine or chlorine, or represents in each case straight-chain or branched cyanoalkyl having 1 to 4 carbon atoms in the alkyl moiety, hydroxyalkyl having 1 to 6 carbon atoms and 1 to 3 hydroxyl groups, alkoxyalkyl, alkoximinoalkyl, alkoxycarbonylalkyl or alkoxycarbonylalkenyl, alkylaminoalkyl or dialkylaminoalkyl, each of which has up to 4 carbon atoms in the individual alkyl or alkenyl moieties, or represents cyclopropyl, cyclopropylmethyl, cyclopropylethyl, cyclobutyl, cyclopentyl, cyclohexyl, cycloheptyl, cyclooctyl, cyclopentylmethyl, cyclohexylmethyl, cyclohexylethyl, cyclohexenyl or cyclohexenylmethyl, each of which is optionally monosubstituted to trisubstituted by identical or different substituents, the following being selected as particularly preferred substituents in the cyclic and if appropriate in the aliphatic moiety: fluorine, chlorine, bromine, methyl, ethyl, n- or i-propyl, n-, i-, s- or t-butyl, cyano, methanediyl, ethanediyl, butanediyl or butadienediyl; $R^1$ furthermore represents heterocyclylmethyl, heterocyclylethyl or heterocyclylpropyl, each of which is optionally monosubstituted to trisubstituted in the heterocyclyl moiety by identical or different substituents, suitable heterocycles in each case being:

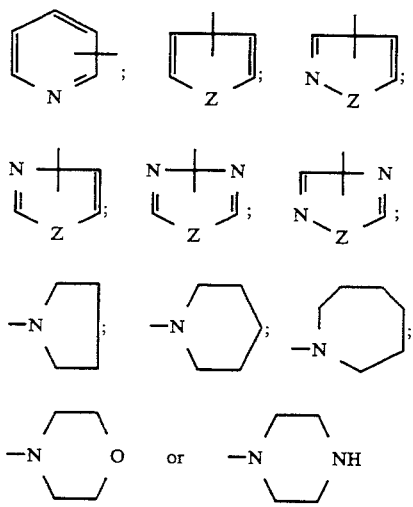

where Z in each case represents oxygen or sulphur and where the following are selected as particularly preferred substituents: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio; R¹ furthermore represents in each case straight-chain or branched alkoxy having 1 to 6 carbon atoms, alkenyloxy having 3 to 6 carbon atoms or alkinyloxy having 3 to 6 carbon atoms, or represents benzyl, phenylethyl, phenylpropyl, phenylbutyl, phenylpentyl, phenylhexyl, phenylheptyl, phenylcyanomethyl, phenylcyanoethyl, phenylcyanopropyl, phenoxymethyl, phenoxyethyl, phenoxypropyl, phenoxybutyl, phenylethinyl, benzyloxy, phenylethyloxy, phenoxy, benzoyl, phenyl or naphthyl, if appropriate straight-chain or branched, each of which is optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, difluoromethoxy, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl and phenoxy, R² represents methyl, ethyl, n- or i-propyl, n-, i-, s-or t-butyl, n- or i-pentyl, n- or i-hexyl, or represents allyl, propargyl, methoxy, ethoxy, methoxymethyl, ethoxymethyl, methoxyethyl or ethoxyethyl, or represents straight-chain or branched halogenoalkyl, halogenoalkenyl and halogenoalkinyl having 1 to 4 carbon atoms and 1 to 9 identical or different halogen atoms, in particular fluorine, chlorine or bromine, or represents cyclopentyl, cyclohexyl, cyclopropyl, cyclopropylmethyl, cyclopentylmethyl, cyclohexylmethyl or cyclohexylethyl, R³ represents methyl, ethyl, n- or i-propyl, n-, i-, s-or t-butyl, n-, i-, s- or t-pentyl, n- or i-hexyl, or represents allyl, propargyl, methoxyethyl, ethoxyethyl, fluoroethyl, chloroethyl, fluoropropyl, chloropropyl or cyanoethyl, X represents oxygen or sulphur and
Y represents oxygen or sulphur.

Very particularly preferred compounds of the formula (I) are those in which

R¹ represents methyl, ethyl, n- or i-propyl, n-, i-, s-or t-butyl, n-, i-, s- or t-pentyl, n-, i-, s- or t-hexyl, propargyl, n- or i-butinyl, n- or i-pentinyl, or represents straight-chain or branched halogenoalkyl having 1 to 4 carbon atoms and 1 to 4 identical or different halogen atoms, in particular fluorine and chlorine, or represents cyanomethyl, cyanoethyl or n- or i-cyanopropyl, or represents cyclopropyl, cyclopropylmethyl, cyclopentyl, cyclopentylmethyl, cyclohexyl or cyclohexylmethyl, each of which is optionally monosubstituted to trisubstituted by identical or different substituents, or represents phenyl, benzyl or phenylethyl, each of which is optionally monosubstituted to trisubstituted by identical or different substituents from the series comprising fluorine, chlorine, bromine, methyl, ethyl and/or trifluoromethyl, or represents in each case straight-chain or branched phenylpropyl, phenylbutyl, phenylpentyl or phenylhexyl, or represents morpholinyl-$C_1$-$C_4$-alkyl, R² represents methyl, ethyl, n-, i- or cyclopropyl, n-, i-, s- or t-butyl, R³ represents methyl, ethyl, n- or i-propyl, n-, i-, s-or t-butyl, n- or i-pentyl, X represents oxygen and
Y represents oxygen.

Examples of the compounds of the formula (I) according to the invention are listed in Table 1 below.

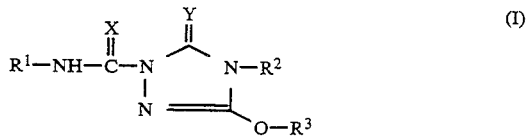

TABLE 1

| Examples of the compounds of the formula (I) | | | | |
|---|---|---|---|---|
| R¹ | R² | R³ | X | Y |
| i-C₃H₇ | CH₃ | CH₃ | O | O |
| CF₃—C(CH₃)₂— | CH₃ | C₂H₅ | O | O |
| F—CH₂—C(CH₃)₂— | CH₃ | C₂H₅ | O | O |
| C₂H₅—C(CH₃)₂— | CH₃ | CH₃ | O | O |
| C₃H₇—C(CH₃)₂— | CH₃ | CH₃ | O | O |
| i-C₃H₇—C(CH₃)₂— | CH₃ | CH₃ | O | O |
| ⟨phenyl⟩—C(CH₃)₂— | CH₃ | CH₃ | O | O |
| ⟨phenyl⟩—CH₂—C(CH₃)₂— | CH₃ | CH₃ | O | O |
| ⟨phenyl⟩—(CH₂)₂—C(CH₃)₂— | CH₃ | CH₃ | O | O |
| ⟨phenyl⟩—(CH₂)₂—C(CH₃)₂— | CH₃ | CH₃ | O | O |
| ⟨phenyl⟩—CH₂—C(CH₃)₂— | CH₃ | CH₃ | O | O |
| ⟨phenyl⟩—C(CH₃)₂— | CH₃ | CH₃ | O | O | course of the reaction of process (c) according to the invention can be illustrated by the following equation:

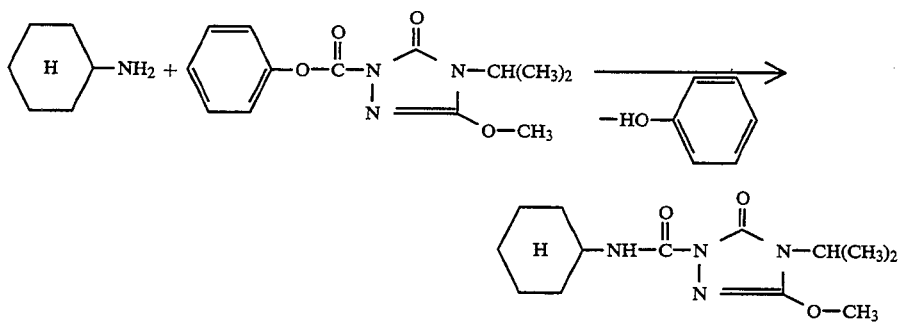

Formula (II) provides a general definition of the 5-alkoxy-1,2,4-triazol-3-(thi)ones to be used as starting substances in processes (a) and (b) according to the invention for the preparation of compounds of the formula (I).

In formula (II), $R^2$, $R^3$ and Y preferably, or in particular, have those meanings which have already been mentioned above in connection with the description of the compounds of the formula (I) according to the invention as being preferred, or as particularly preferred, for $R^2$, $R^3$ and Y.

Examples of the starting substances of the formula (II) are listed in Table 2 below.

Examples of the compounds of the formula (I)

| $R^1$ | $R^2$ | $R^3$ | X | Y |
|---|---|---|---|---|
| ⟨phenyl⟩—C(CH₃)₂— | CH₃ | C₂H₅ | O | O |
| CH₃O—⟨phenyl⟩—CH₂—CH₂—C(CH₃)₂— | CH₃ | CH₃ | O | O |

If, for example, 5-ethoxy-4-ethyl-2,4-dihydro-3H-1,2,4-triazole-3-thione and isopropyl-isocyanate are used as starting substances, the course of the reaction of process (a) according to the invention can be illustrated by the following equation:

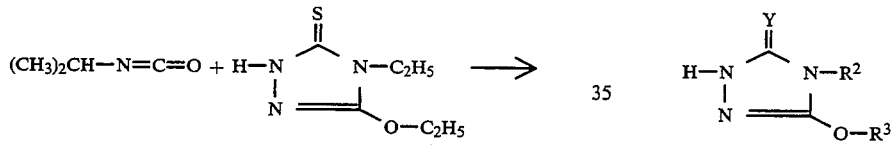

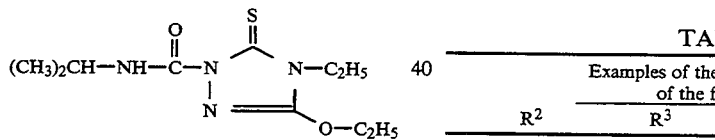

If, for 1 example, 5-isopropoxy-4-methyl-2,4-dihydro-3H-1,2,4-triazol-3-one and O-Methyl-N-tert.-butylthiocarbamate are used as starting substances, the course of the reaction of process (b) according to the invention can be illustrated by the following equation:

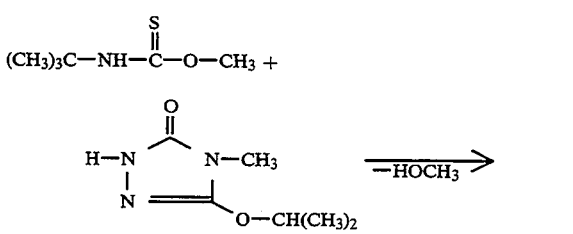

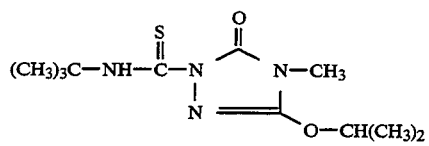

If, for example, 4-isopropyl-5-methoxy-2-phenoxycarbonyl-2,4-dihydro-3H-1,2,4-triazol-3-one and cyclohexylamine are used as starting substances, the $$H-N\overset{Y}{\underset{N}{\diagdown}}\diagup N-R^2 \quad \quad \text{(II)}$$
$$\quad \quad \diagdown O-R^3$$

TABLE 2

| Examples of the starting substances of the formula (II) | | |
|---|---|---|
| $R^2$ | $R^3$ | Y |
| CH₃ | CH₃ | O |
| CH₃ | CH₃ | S |
| CH₃ | C₂H₅ | O |
| CH₃ | C₂H₅ | S |
| CH₃ | C₃H₇ | O |
| CH₃ | C₃H₇ | S |
| CH₃ | CH(CH₃)₂ | O |
| CH₃ | CH(CH₃)₂ | S |
| CH₃ | —CH₂—CH=CH₂ | O |
| CH₃ | —CH₂—CH=CH₂ | S |
| C₂H₅ | CH₃ | O |
| C₂H₅ | CH₃ | S |
| C₂H₅ | C₂H₅ | O |
| C₂H₅ | C₂H₅ | S |
| C₂H₅ | CH(CH₃)₂ | O |
| C₂H₅ | —CH₂—CH=CH₂ | O |
| C₂H₅ | CH(CH₃)₂ | S |
| C₂H₅ | —CH₂—CH=CH₂ | S |

The starting substances of the formula (II) are known in some cases (cf. J. Chem. Soc C 1967, 2700–2704; J. Heterocycl. Chem. 15 (1978), 377–384).

Those compounds of the general formula (II) in which Y represents oxygen and $R^2$ and $R^3$ have the abovementioned meanings are new and are a subject of the present patent application.

The new 5-alkoxy-1,2,4-triazol-3-ones (II, Y=O) are obtained when hydrazinoformic esters of the general formula (VII)

$$H_2N-NH-CO-O-R^4 \quad \text{(VII)}$$

in which

R⁴ has the abovementioned meaning are reacted with alkyliminocarboxylic diesters of the general formula (VIII)

$$R^2-N=C{\overset{O-R^3}{\underset{O-R^3}{}}} \quad \text{(VIII)}$$

in which

R² and R³ have the abovementioned meaning, if appropriate in the presence of a diluent such as, for example, o-dichlorobenzene, at temperatures between 0° C. and 200° C., preferably between 50° C. and 150° C. (cf. the Preparation Examples).

The starting substances of the formulae (VII) and (VIII) are known chemicals.

Formula (III) provides the general definition of the iso (thio) cyanates to be used as starting substances in process (a) according to the invention for the preparation of compounds of the formula (I).

In formula (III), R¹ and X preferably, or in particular, have those meanings which have already been mentioned above in connection with the description of the compounds of the formula (I) according to the invention as being preferred, or as particularly preferred, for R¹ and X.

The starting substances of the formula (III) are known chemicals for organic synthesis.

Formula (IV) provides a general definition of the reactive (thio)carbamates to be used as starting substances in process (b) according to the invention for the preparation of compounds of the formula (I).

In formula (IV), R¹ and X preferably, or in particular, have those meanings which have already been mentioned above in connection with the description of the compounds of the formula (I) according to the invention as being preferred, or as particularly preferred, for R¹ and X;

R⁴ preferably represents methyl, ethyl, phenyl or benzyl.

The starting substances of the formula (IV) are known chemicals for organic synthesis.

Formula (V) provides a general definition of the 5-alkoxy-1,2,4-triazol-3-(thi)one derivatives to be used as starting substances in process (c) according to the invention for the preparation of compounds of the formula (I).

In formula (V), R², R³, X and Y preferably, or in particular, have those meanings which have already been mentioned above in connection with the description of the compounds of the formula (I) according to the invention as being preferred, or as particularly preferred, for R², R³, X and Y;

R⁴ preferably represents methyl, ethyl, phenyl or benzyl.

The starting substances of the formula (V) were hitherto not known from the literature and are a subject of the present patent application.

The new 5-alkoxy-1,2,4-triazol-3-(thi)one derivatives of the general formula (V) are obtained when 5-alkoxy-1,2,4-triazol-3-(thi)ones of the general formula (II)

$$\underset{N}{\overset{Y}{\underset{\|}{H-N}}}\underset{=}{\overset{}{}}\underset{O-R^3}{\overset{N-R^2}{}} \quad \text{(II)}$$

in which

R², R³ and Y have the abovementioned meanings are reacted with chloro(thio)formic esters of the general formula (IX)

$$R^4-O-\overset{X}{\underset{\|}{C}}-Cl \quad \text{(IX)}$$

in which

R⁴ and X have the abovementioned meanings, if appropriate in the presence of a diluent such as, for example, tetrahydrofuran, and if appropriate in the presence of an acid acceptor such as, for example, potassium tert-butylate, at temperatures between −20° C. and +100° C.

Formula (VI) provides a general definition of the amino compounds furthermore to be used as starting substances in process (c) according to the invention for the preparation of compounds of the formula (I).

In formula (VI), R¹ preferably, or in particular, has the meaning which has already been mentioned above in connection with the description of the compounds of the formula (I) according to the-invention as being preferred, or as particularly preferred, for R¹.

The starting substances of the formula (VI) are known chemicals for organic synthesis.

Processes (a), (b) and (c) according to the invention for the preparation of the new compounds of the formula (I) are preferably carried out in each case using diluents. Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

If appropriate, processes (a), (b) and (c) according to the invention are in each case carried out in the presence of a basic reaction auxiliary. Suitable substances which are employed are preferably basic organic nitrogen compounds. These include, for example, trimethylamine, triethylamine, tripropylamine, tributylamine, diisopropylamine, dicyclohexylamine, N,N-dimethylaniline, N,N-dimethylbenzylamine, pyridine, 4-dimethylamino-pyridine, 1,5-diazabicyclo-(4,3,0]-non-5-ene(DBN), 1,8-diazabicyclo[5,4,0)-undec-7-ene (DBU) and 1,4-diazabicyclo-[2,2,2]-octane (DABCO).

When carrying out processes (a), (b) and (c) according to the invention, the reaction temperatures can be varied in each case in a substantial range. In general, the processes are carried out at temperatures between −20° C. and +150° C., preferably at temperatures between 0° C. and 100° C.

In general, processes (a), (b) and (c) according to the invention are carried out under atmospheric pressure. However, it is also possible to carry out the processes under increased or reduced pressure.

For carrying out processes (a), (b) and (c) according to the invention, the starting substances required in each case are generally employed in approximately equimolar amounts. However, it is also possible to use one of the two-components employed in each case in a larger excess. In general, the reactions are carried out in a suitable diluent in the presence of a basic reaction auxiliary, and the reaction mixture is stirred for several hours at the particular temperature required. Working-up in the processes according to the invention is carried out in each case by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The compounds of the formula (I) according to the invention are suitable for selectively combating monocotyledon and dicotyledon weeds, mainly in monocotyledon cultures, by the pre- and the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 2-chloro-2',6'-diethyl-N-methoxy-methylacetanilide (ALACHLOR); methyl-6,6-dimethyl-2,4-dioxo-3-[1-(2-propenyloxyamino)-butylidene]-cyclohexanecarboxylic acid (ALLOXYDIM); 4-aminobenzenesulphonyl methyl carbamate (ASULAM); 2-chloro-4-ethylamino-6-isopropylamino-1,3,5-triazine (ATRAZINE); methyl 2-[[[[(4,6-dimethoxypyrimidin-2-yl)-amino]-carbonyl]-amino]-sulphonyl]-methyl]-benzoate (BENSULFURON); 3-isopropyl-2,1,3-benzothiadiazin-4-one-2,2-dioxide (BENTAZONE); 3,5-dibromo-4-hydroxy-benzonitrile (BROMOXYNIL); N-(butoxymethyl)-2-chloro-N-(2,6-diethylphenyl)-acetamide (BUTACHLOR); 5-amino-4-chloro-2-phenyl-2,3-dihydro-3-oxy-pyridazine (CHLORIDAZONE); isopropyl N-(3-chlorophenyl)-carbamate (CHLORPROPHAM); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); N,S-diethyl N-cyclohexyl-thiolcarbamate (CYCLOATE); 2-[1-(ethoximino)-butyl]-3-hydroxy-5-[tetrahydro-(2H)-thiopyran-3-yl]-2-cyclohexane-1-one (CYCLOXYDIM); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamidate (EPTAME); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or its 1-methylheptyl ester (FLUROXYPYR); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); S-ethyl N,N-hexamethylenethiocarbamate (MOLINATE); 1-(3-trifluoromethylphenyl)-4-methylamino-5-chloro-6-pyridazone (NORFLURAZON); 4-(di-n-propylamino)-3,5-dinitrobenzenesulphonamide (ORYZALIN); N-(1-ethylpropyl)-3,4-dimethyl-2,6-dinitroaniline (PENDIMETHALIN); 3-(ethoxycarbonylaminophenyl)-N-(3'-methylphenyl)-carbamate (PHENMEDIPHAM); 2-chloro-N-isopropylacetanilide (PROPACHLOR); isopropyl N-phenyl-carbamate (PROPHAM); O-(6-chloro-3-phenyl-pyridazin-4-yl) S-octyl thiocarbonate (PYRIDATE); ethyl 2-[4-(6-chloroquinoxalin-2-yl-oxy)-phenoxy]-propionate (QUIZALOFOPETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-[(4-chlorophenyl)methyl]N,N-diethylthiocarbamate (THIOBENCARB); S-(2,3,3-trichloroallyl)N,N-diisopropylthiocarbamate (TRIALLATE); 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 10 g and 5 kg per ha.

The preparation and use of the active compounds according to the invention can be seen from the following examples.

PREPARATION EXAMPLES
EXAMPLE 1

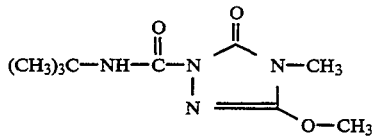

A mixture of 1.3 g (0.01 mol) of 5-methoxy-4-methyl-2,4-dihydro-3H-1,2,4-triazol-3-one, 0.1 g of 1,8-diazabicyclo[5.4.0]undec-7-ene (DBU), 1.0 g (0.01 mol) of tertbutyl isocyanate and 50 ml of acetonitrile is stirred for 12 hours at 20° C. and subsequently concentrated under a water pump vacuum. The residue is taken up in methylene chloride, and the mixture is washed with water, dried with magnesium sulphate and filtered. The filtrate is concentrated under a water pump vacuum, the residue is brought to crystallisation by trituration with petroleum ether, and the product is isolated by filtration with suction.

1.4 g (61% Of theory) of 2-tert-butyl-amino-carbonyl-5-methoxy-4-methyl-2,4-dihydro-3H-1,2,4-triazol-3-one of melting point 167° C. are obtained.

Other examples of the compounds of the formula (I) which can be prepared analogously to Example 1 and corresponding to the general description of the preparation processes according to the invention are those listed in Table 3 below.

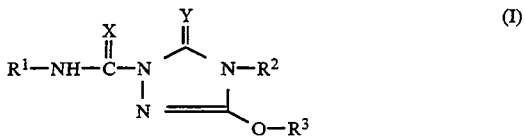

(I)

TABLE 3

Preparation examples of the compounds of the formula (I)

| Example No. | $R^1$ | $R^2$ | $R^3$ | X | Y | Melting point (°C.) |
|---|---|---|---|---|---|---|
| 2 | ClCH$_2$C(CH$_3$)$_2$— | CH$_3$ | CH$_3$ | O | O | 153 |
| 3 | H$_3$CO—C$_6$H$_4$—OCH$_2$CH(CH$_3$)— | C$_3$H$_7$ | CH$_3$ | O | O | (oil) |
| 4 | Cl—C$_6$H$_4$—CH$_2$CH$_2$C(CH$_3$)$_2$— | C$_3$H$_7$ | CH$_3$ | O | O | (oil) |
| 5 | Cl—C$_6$H$_4$—CH$_2$CH$_2$C(CH$_3$)$_2$— | CH$_3$ | C$_2$H$_5$ | O | O | (oil) |
| 6 | Cl—C$_6$H$_4$—CH$_2$CH$_2$C(CH$_3$)$_2$— | C$_2$H$_5$ | CH$_3$ | O | O | (oil) |
| 7 | Cl—C$_6$H$_4$—CH$_2$CH(CH$_3$)—CH(CH$_3$)— | CH$_3$ | C$_2$H$_5$ | O | O | (oil) |
| 8 | F—C$_6$H$_4$—CH$_2$CH$_2$CH(CH$_3$)— | CH$_3$ | C$_2$H$_5$ | O | O | (oil) |
| 9 | H$_3$C—C$_6$H$_4$—CH$_2$CH$_2$CH(CH$_3$)— | CH$_3$ | C$_2$H$_5$ | O | O | (oil) |
| 10 | C$_6$H$_5$—CH$_2$CH$_2$CH(CH$_3$)— | CH$_3$ | C$_2$H$_5$ | O | O | (oil) |

TABLE 3-continued

| Example No. | R¹ | R² | R³ | X | Y | Melting point (°C.) |
|---|---|---|---|---|---|---|
| 11 | H₃CO—⟨C₆H₄⟩—OCH₂CH(CH₃)— | CH₃ | C₂H₅ | O | O | (oil) |
| 12 | Cl—⟨C₆H₄⟩—CH₂CH(C₂H₅)—CH(CH₃) | CH₃ | C₂H₅ | O | O | (oil) |
| 13 | Cl—⟨C₆H₄⟩—CH₂CH₂CH(CH₃)— | CH₃ | C₂H₅ | O | O | (oil) |
| 14 | H—⟨C₆H₁₁⟩—C(CH₃)₂— | CH₃ | CH₃ | O | O | 166 |
| 15 | H—⟨C₆H₁₁⟩—CH₂CH₂C(CH₃)₂— | CH₃ | CH₃ | O | O | 120 |
| 16 | ⟨C₆H₅⟩—C(CH₃)₂— | CH₃ | CH₃ | O | O | 176 |
| 17 | Cl—⟨C₆H₄⟩—C(CH₃)₂CH₂CH₂— | CH₃ | CH₃ | O | O | 130 |
| 18 | 2,4-Cl₂—⟨C₆H₃⟩—CH(CH₃)— | CH₃ | CH₃ | O | O | 104 |
| 19 | ⟨C₆H₅⟩—CH₂CH₂C(CH₃)₂— | CH₃ | CH₃ | O | O | 117 |
| 20 | H₃C—⟨C₆H₄⟩—CH(CH₃)— | CH₃ | CH₃ | O | O | 100 |
| 21 | (CH₃)₃C— | CH₃ | C₃H₇ | O | O | 75 |
| 22 | ClCH₂C(CH₃)₂— | CH₃ | C₃H₇ | O | O | 95 |
| 23 | ⟨C₆H₅⟩—CH₂C(CH₃)₂— | CH₃ | CH₃ | O | O | 142 |

TABLE 3-continued

Preparation examples of the compounds of the formula (I)

| Example No. | R¹ | R² | R³ | X | Y | Melting point (°C.) |
|---|---|---|---|---|---|---|
| 24 | 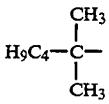 | CH₃ | CH₃ | O | O | 135 |
| 25 | 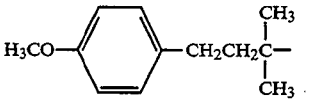 | CH₃ | CH₃ | O | O | 106 |
| 26 | 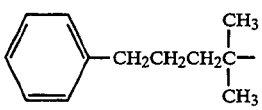 | CH₃ | CH₃ | O | O | 137 |
| 27 | 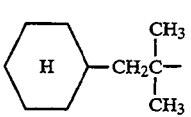 | CH₃ | CH₃ | O | O | 131 |
| 28 | 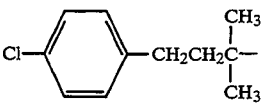 | CH₃ | CH₃ | O | O | 118 |
| 29 | 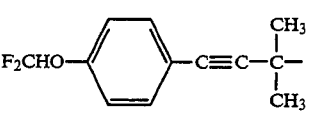 | CH₃ | CH₃ | O | O | 82 |
| 30 | (CH₃)₃C— | CH₂—CH=CH₂ | CH₃ | O | O | 87 |
| 31 | (CH₃)₃C— | n-C₃H₇ | CH₃ | O | O | 144 |
| 32 | (CH₃)₃C— | CH₃ | C₂H₅ | O | O | 102–103 |
| 33 | (CH₃)₃C— | CH₃ | C₄H₉-n | O | O | 79–80 |
| 34 | (CH₃)₃C— |  | C₂H₅ | O | O | 108 |
| 35 | (CH₃)₃C— | C₂H₅ | CH₃ | O | O | 144–146 |
| 36 | (CH₃)₃C— | CH₂—CH=CH₂ | C₂H₅ | O | O | 63–64 |
| 37 | (CH₃)₃C— | i-C₃H₇ | C₂H₅ | O | O | 68–69 |
| 38 | (CH₃)₃C— | (CH₂)₃—OCH₃ | CH₃ | O | O | 86–87 |
| 39 | (CH₃)₃C— | n-C₃H₇ | C₂H₅ | O | O | 70–71 |
| 40 | 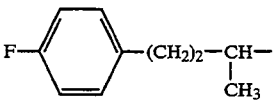 | CH₃ | C₄H₉-n | O | O | Oil |
| 41 | 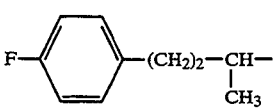 |  | C₂H₅ | O | O | Oil |
| 42 | 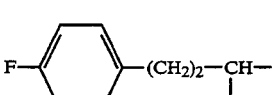 | C₂H₅ | CH₃ | O | O | Oil |
| 43 | 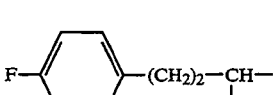 | CH₃ | i-C₃H₇ | O | O | Oil |

TABLE 3-continued

Preparation examples of the compounds of the formula (I)

| Example No. | R$^1$ | R$^2$ | R$^3$ | X | Y | Melting point (°C.) |
|---|---|---|---|---|---|---|
| 44 | 4-F-C$_6$H$_4$-(CH$_2$)$_2$-CH(CH$_3$)- | n-C$_3$H$_7$ | CH$_3$ | O | O | 78 |
| 45 | 4-F-C$_6$H$_4$-(CH$_2$)$_2$-CH(CH$_3$)- | CH$_2$CH=CH$_2$ | C$_2$H$_5$ | O | O | Oil |
| 46 | 4-F-C$_6$H$_4$-(CH$_2$)$_2$-CH(CH$_3$)- | n-C$_3$H$_7$ | CH$_3$ | O | O | 93–94 |
| 47 | 4-Cl-C$_6$H$_4$-(CH$_2$)$_2$-CH(CH$_3$)- | CH$_3$ | C$_4$H$_9$-n | O | O | Oil |
| 48 | 4-Cl-C$_6$H$_4$-(CH$_2$)$_2$-CH(CH$_3$)- | cyclopropyl | C$_2$H$_5$ | O | O | Oil |
| 49 | 4-Cl-C$_6$H$_4$-(CH$_2$)$_2$-CH(CH$_3$)- | C$_2$H$_5$ | CH$_3$ | O | O | Oil |
| 50 | 4-Cl-C$_6$H$_4$-(CH$_2$)$_2$-CH(CH$_3$)- | CH$_2$—CH=CH$_2$ | C$_2$H$_5$ | O | O | Oil |
| 51 | 4-Cl-C$_6$H$_4$-(CH$_2$)$_2$-CH(CH$_3$)- | i-C$_3$H$_7$ | C$_2$H$_5$ | O | O | Oil |
| 52 | 4-Cl-C$_6$H$_4$-(CH$_2$)$_2$-CH(CH$_3$)- | (CH$_2$)$_3$—OCH$_3$ | CH$_3$ | O | O | 104–105 |
| 53 | 4-Cl-C$_6$H$_4$-(CH$_2$)$_2$-CH(CH$_3$)- | n-C$_3$H$_7$ | C$_2$H$_5$ | O | O | Oil |
| 54 | 4-Cl-C$_6$H$_4$-(CH$_2$)$_2$-CH(CH$_3$)- | i-C$_3$H$_7$ | CH$_3$ | O | O | Oil |
| 55 | 4-Cl-C$_6$H$_4$-(CH$_2$)$_2$-CH(CH$_3$)- | CH$_3$ | i-C$_3$H$_7$ | O | O | Oil |

TABLE 3-continued

Preparation examples of the compounds of the formula (I)

| Example No. | R¹ | R² | R³ | X | Y | Melting point (°C.) |
|---|---|---|---|---|---|---|
| 56 | CH₃—C₆H₄—(CH₂)₂—C(CH₃)₂— | n-C₃H₇ | CH₃ | O | O | Oil |
| 57 | CH₃—C₆H₄—(CH₂)₂—C(CH₃)₂— | CH₃ | C₂H₅ | O | O | Oil |
| 58 | CH₃—C₆H₄—(CH₂)₂—C(CH₃)₂— | C₂H₅ | CH₃ | O | O | Oil |
| 59 | CH₃—C₆H₄—(CH₂)₂—C(CH₃)₂— | CH₂—CH=CH₂ | C₂H₅ | O | O | Oil |
| 60 | CH₃—C₆H₄—(CH₂)₂—C(CH₃)₂— | n-C₃H₇ | C₂H₅ | O | O | Oil |
| 61 | CH₃—C₆H₄—(CH₂)₂—C(CH₃)₂— | i-C₃H₇ | CH₃ | O | O | Oil |
| 62 | CH₃—C₆H₄—(CH₂)₂—C(CH₃)₂— | CH₃ | i-C₃H₇ | O | O | Oil |
| 63 | CF₃—C₆H₄—(CH₂)₂—C(CH₃)₂— | n-C₃H₇ | CH₃ | O | O | Oil |
| 64 | CF₃—C₆H₄—(CH₂)₂—C(CH₃)₂— | CH₃ | C₂H₅ | O | O | Oil |
| 65 | CF₃—C₆H₄—(CH₂)₂—C(CH₃)₂— | CH₃ | n-C₄H₉ | O | O | Oil |
| 66 | CF₃—C₆H₄—(CH₂)₂—C(CH₃)₂— | C₂H₅ | CH₃ | O | O | Oil |
| 67 | CF₃—C₆H₄—(CH₂)₂—C(CH₃)₂— | n-C₃H₇ | C₂H₅ | O | O | Oil |
| 68 | CF₃—C₆H₄—(CH₂)₂—C(CH₃)₂— | i-C₃H₇ | CH₃ | O | O | Oil |

TABLE 3-continued

Preparation examples of the compounds of the formula (I)

| Example No. | R¹ | R² | R³ | X | Y | Melting point (°C.) |
|---|---|---|---|---|---|---|
| 69 | F–C₆H₄–(CH₂)₂–C(CH₃)₂– | n-C₃H₇ | CH₃ | O | O | Oil |
| 70 | F–C₆H₄–(CH₂)₂–C(CH₃)₂– | CH₃ | C₂H₅ | O | O | Oil |
| 71 | F–C₆H₄–(CH₂)₂–C(CH₃)₂– | CH₃ | n-C₄H₉ | O | O | Oil |
| 72 | F–C₆H₄–(CH₂)₂–C(CH₃)₂– | C₂H₅ | CH₃ | O | O | Oil |
| 73 | F–C₆H₄–(CH₂)₂–C(CH₃)₂– | n-C₃H₇ | C₂H₅ | O | O | Oil |
| 74 | 3-CF₃-4-CH₃-C₆H₃–(CH₂)₂–C(CH₃)₂– | n-C₃H₇ | CH₃ | O | O | Oil |
| 75 | 3-CF₃-4-CH₃-C₆H₃–(CH₂)₂–C(CH₃)₂– | CH₃ | C₂H₅ | O | O | Oil |
| 76 | 3-CF₃-4-CH₃-C₆H₃–(CH₂)₂–C(CH₃)₂– | C₂H₅ | CH₃ | O | O | Oil |
| 77 | 3-CF₃-4-CH₃-C₆H₃–(CH₂)₂–C(CH₃)₂– | CH₂–CH=CH₂ | C₂H₅ | O | O | Oil |
| 78 | 3-CF₃-4-CH₃-C₆H₃–(CH₂)₂–C(CH₃)₂– | n-C₃H₇ | C₂H₅ | O | O | Oil |
| 79 | 3-Cl-C₆H₄–(CH₂)₂–C(CH₃)₂– | n-C₃H₇ | CH₃ | O | O | 107–108 |

TABLE 3-continued
Preparation examples of the compounds of the formula (I)
| Example No. | R¹ | R² | R³ | X | Y | Melting point (°C.) |
|---|---|---|---|---|---|---|
| 80 |  3-Cl-C6H4-(CH2)2-C(CH3)2- | CH3 | C4H9-n | O | O | Oil |
| 81 | 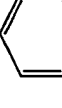 3-Cl-C6H4-(CH2)2-C(CH3)2- | C2H5 | CH3 | O | O | 83–85 |
| 82 | 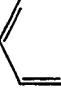 3-Cl-C6H4-(CH2)2-C(CH3)2- | n-C3H7 | C2H5 | O | O | 125–127 |
| 83 | 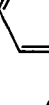 3-Cl-C6H4-(CH2)2-C(CH3)2- | i-C3H7 | CH3 | O | O | 108–110 |
| 84 | 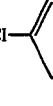 4-Cl-C6H4-C(CH3)2-CH2-CH(CH3)- | n-C3H7 | CH3 | O | O | 100–102 |
| 85 |  2-(COOCH3)-C6H4- | CH3 | C2H5 | O | O | 164–166 |
| 86 | 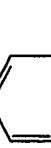 2-(COOCH3)-C6H4- | CH3 | n-C4H9 | O | O | 145 |
| 87 | 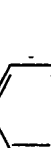 2-(COOCH3)-C6H4- | n-C3H7 | CH3 | O | O | 109–110 |
| 88 | 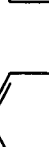 2-(COOCH3)-C6H4- |  cyclopropyl | C2H5 | O | O | 123–125 |
| 89 | 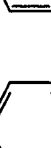 2-(COOCH3)-C6H4- | n-C3H7 | C2H5 | O | O | 95–98 |
| 90 |  4-Cl-C6H4-C(CH3)2-CH2-CH(CH3)- | CH3 | C2H5 | O | O | 90–91 |

TABLE 3-continued

Preparation examples of the compounds of the formula (I)

| Example No. | R$^1$ | R$^2$ | R$^3$ | X | Y | Melting point (°C.) |
|---|---|---|---|---|---|---|
| 91 | 2-Cl-C$_6$H$_4$-(CH$_2$)$_2$-C(CH$_3$)$_2$- | CH$_3$ | C$_2$H$_5$ | O | O | 64–66 |
| 92 | 4-Cl-C$_6$H$_4$-(CH$_2$)-C(C$_2$H$_5$)$_2$- | CH$_3$ | C$_2$H$_5$ | O | O | 84–85 |
| 93 | C$_6$H$_5$-(CH$_2$)$_2$-C(C$_2$H$_5$)$_2$- | CH$_3$ | C$_2$H$_5$ | O | O | 104–105 |
| 94 | 2,6-Cl$_2$-C$_6$H$_3$-(CH$_2$)$_2$-C(CH$_3$)$_2$- | CH$_3$ | C$_2$H$_5$ | O | O | 113–116 |
| 95 | 2-thienyl-C≡C-(C(CH$_3$)$_2$)- | cyclopropyl | C$_2$H$_5$ | O | O | 95 |
| 96 | 3-CN-C$_6$H$_4$-(CH$_2$)$_2$-C(CH$_3$)$_2$- | CH | C$_2$H$_5$ | O | O | 115–116 |
| 97 | (CH$_3$)$_3$C— | CH$_3$ | i-C$_3$H$_7$ | O | O | 82–84 |
| 98 | Cl—CH$_2$—C(CH$_3$)$_2$— | n-C$_3$H$_7$ | CH$_3$ | O | O | 93–95 |
| 99 | Cl—CH$_2$—C(CH$_3$)$_2$— | CH$_3$ | n-C$_4$H$_9$ | O | O | 85–87 |
| 100 | Cl—CH$_2$—C(CH$_3$)$_2$— | C$_2$H$_5$ | CH$_3$ | O | O | 127–129 |
| 101 | Cl—CH$_2$—C(CH$_3$)$_2$— | CH$_2$—CH=CH$_2$ | C$_2$H$_5$ | O | O | Oil |
| 102 | Cl—CH$_2$—C(CH$_3$)$_2$— | n-C$_3$H$_7$ | C$_2$H$_5$ | O | O | 63–65 |
| 103 | Cl—CH$_2$—C(CH$_3$)$_2$— | CH$_3$ | i-C$_3$H$_7$ | O | O | 85–87 |
| 104 | Cl—CH$_2$—C(CH$_3$)$_2$— | CH$_3$ | C$_2$H$_5$ | O | O | 95–96 |
| 105 | 2-COOCH$_3$-C$_6$H$_4$- | CH$_3$ | i-C$_3$H$_7$ | O | O | 146 |
| 106 | 4-Cl-C$_6$H$_4$-CH$_2$-CH(C$_2$H$_5$)-CH(CH$_3$)- | CH$_3$ | i-C$_3$H$_7$ | O | O | Oil |
| 107 | 2-Cl-C$_6$H$_4$-(CH$_2$)$_2$-CH(CH$_3$)- | CH$_3$ | i-C$_3$H$_7$ | O | O | Oil |
| 108 | 4-F-C$_6$H$_4$-O-CH$_2$-C(CH$_3$)$_2$-CH(CH$_3$)- | CH$_3$ | i-C$_3$H$_7$ | O | O | Oil |

TABLE 3-continued

Preparation examples of the compounds of the formula (I)

| Example No. | $R^1$ | $R^2$ | $R^3$ | X | Y | Melting point (°C.) |
|---|---|---|---|---|---|---|
| 109 | F–⟨C6H4⟩–O–CH2–C(CH3)2–CH(CH3)– | $CH_3$ | $C_2H_5$ | O | O | 115–117 |
| 110 | F–⟨C6H4⟩–O–CH2–C(CH3)2–CH(CH3)– | $C_2H_5$ | $CH_3$ | O | O | 129–130 |
| 111 | F–⟨C6H4⟩–O–CH2–C(CH3)2–CH(CH3)– | cyclopropyl | $C_2H_5$ | O | O | Oil |
| 112 | $(CH_3)_3C-$ | $CH_3$ | $(CH_2)_2-OC_2H_5$ | O | O | 58 |
| 113 | $Cl-CH_2-C(CH_3)_2-$ | $CH_3$ | $(CH_2)_2-OC_2H_5$ | O | O | Oil |
| 114 | 2-(COOCH3)-C6H4– | $CH_3$ | $(CH_2)_2-OC_2H_5$ | O | O | 126–128 |
| 115 | F–⟨C6H4⟩–(CH2)2–CH(CH3)– | $CH_3$ | $(CH_2)_2-OC_2H_5$ | O | O | Oil |
| 116 | F–⟨C6H4⟩–(CH2)2–CH(CH3)– | $CH_3$ | $(CH_2)_2-OCH_3$ | O | O | Oil |
| 117 | Cl–⟨C6H4⟩–O–CH2–CH(CH3)– | $CH_3$ | $(CH_2)_2-OCH_3$ | O | O | Oil |
| 118 | $n\text{-}C_6H_{13}-CH(CH_3)-$ | $CH_3$ | $CH_3$ | O | O | 83 |
| 119 | $(CH_3)_3C-CH(CH_3)-$ | $CH_3$ | $CH_3$ | O | O | 169 |
| 120 | cyclohexyl–CH(CH3)– | $CH_3$ | $CH_3$ | O | O | 117 |
| 121 | $(CH_3)_2CH-CH_2-$ | $CH_3$ | $CH_3$ | O | O | 120 |
| 122 | cyclohexyl– | $CH_3$ | $CH_3$ | O | O | 171 |
| 123 | $n\text{-}C_3H_7-C(CH_3)_2-$ | $CH_3$ | $CH_3$ | O | O | 147 |
| 124 | cyclopentyl– | $CH_3$ | $CH_3$ | O | O | 139 |

TABLE 3-continued

Preparation examples of the compounds of the formula (I)

| Example No. | R¹ | R² | R³ | X | Y | Melting point (°C.) |
|---|---|---|---|---|---|---|
| 125 | 1-methyl-cyclohexyl (cyclohexyl with CH₃ and H) | $CH_3$ | $CH_3$ | O | O | 165 |
| 126 | $CH_3-C(C_2H_5)_2-$ | $CH_3$ | $CH_3$ | O | O | 149 |
| 127 | $NC-CH_2-CH(C_2H_5)-$ | $CH_3$ | $CH_3$ | O | O | 92 |
| 128 | $n-C_5H_{11}-CH(CH_3)-$ | $CH_3$ | $CH_3$ | O | O | 105 |
| 129 | $(CH_3)_3C-CH_2-CH(CH_3)-$ | $CH_3$ | $CH_3$ | O | O | 104 |
| 130 | 4-tert-butyl-cyclohexyl | $CH_3$ | $CH_3$ | O | O | 182 |
| 131 | $n-C_4H_9-CH(C_2H_5)-CH_2-$ | $CH_3$ | $CH_3$ | O | O | 61 |
| 132 | $(C_2H_5)_3C-$ | $CH_3$ | $CH_3$ | O | O | 148 |
| 133 | $C_2H_5-C(CH_3)_2-$ | $CH_3$ | $CH_3$ | O | O | 151 |
| 134 | 4-ethyl-cyclohexyl | $CH_3$ | $CH_3$ | O | O | 126 |
| 135 | cyclopropyl-CH(CH₃)- | $CH_3$ | $CH_3$ | O | O | 128 |
| 136 | methylcycloheptyl | $CH_3$ | $CH_3$ | O | O | 146 |
| 137 | $n-C_6H_{13}-$ | $CH_3$ | $CH_3$ | O | O | 110 |
| 138 | $(CH_3)_3C-CH_2-C(CH_3)_2-$ | $CH_3$ | $CH_3$ | O | O | 150 |
| 139 | $(CH_3)_2CH-CH(CH_3)-$ | $CH_3$ | $CH_3$ | O | O | 126 |
| 140 | $HC\equiv C-C(CH_3)_2-$ | $CH_3$ | $CH_3$ | O | O | 198 |
| 141 | 1-ethyl-cyclohexyl (cyclohexyl with C₂H₅ and H) | $CH_3$ | $CH_3$ | O | O | 165 |
| 142 | cyclopropyl | $CH_3$ | $CH_3$ | O | O | 154 |
| 143 | $(CH_3)_2CH-CH_2-CH_2-$ | $CH_3$ | $CH_3$ | O | O | 135 |
| 144 | $(CH_3)_2CH-C(CH_3)_2-$ | $CH_3$ | $CH_3$ | O | O | 158 |
| 145 | $Cl_2CH-C(CH_3)_2-$ | $CH_3$ | $CH_3$ | O | O | 153 |

TABLE 3-continued

Preparation examples of the compounds of the formula (I)

| Example No. | R¹ | R² | R³ | X | Y | Melting point (°C.) |
|---|---|---|---|---|---|---|
| 146 | (CH₃)₂CH—CH₂—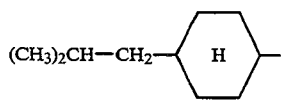— | CH₃ | CH₃ | O | O | 129 |
| 147 | n-C₅H₁₁ | CH₃ | CH₃ | O | O | 107 |
| 148 | (C₂H₅)₂CH—CH₂ | CH₃ | CH₃ | O | O | 91 |
| 149 | C₂H₅—CH—CH₂CH—<br>　　　 \|　　　 \|<br>　　　CH₃　　C₂H₅ | CH₃ | CH₃ | O | O | 85 |
| 150 | (CH₃)₂CH— | CH₃ | CH₃ | O | O | 118 |
| 151 | (Cl—CH₂)₂C(CH₃)— | CH₃ | CH₃ | O | O | 153 |
| 152 | F—CH₂—C(CH₃)₂— | CH₃ | CH₃ | O | O | 151 |
| 153 | 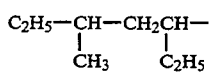 | CH₃ | CH₃ | O | O | 123 |
| 154 | 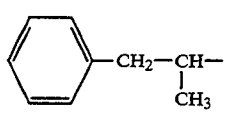 | CH₃ | CH₃ | O | O | 91 |
| 155 | 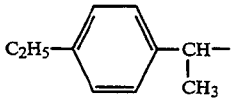 | CH₃ | CH₃ | O | O | 173 |
| 156 | CH₃—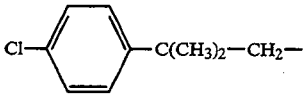— | CH₃ | CH₃ | O | O | 149 |
| 157 | 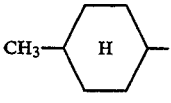 | CH₃ | CH₃ | O | O | 147 |
| 158 | n-C₃H₇—CH—<br>　　　　　\|<br>　　　　CH₃ | CH₃ | CH₃ | O | O | 87 |
| 159 | 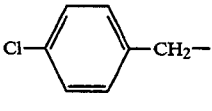 | CH₃ | CH₃ | O | O | 162 |
| 160 | (CH₃)₃C—CH₂—CH—CH₂—CH₂—<br>　　　　　　　　\|<br>　　　　　　　CH₃ | CH₃ | CH₃ | O | O | 60 |
| 161 | n-C₃H₇ | CH₃ | CH₃ | O | O | 108 |
| 162 | 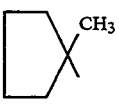 | CH₃ | CH₃ | O | O | 131 |
| 163 | Cl—CH₂—CH₂— | CH₃ | CH₃ | O | O | 117 |
| 164 | C₂H₅—CH—<br>　　　\|<br>　　CH₃ | CH₃ | CH₃ | O | O | 96 |

TABLE 3-continued

Preparation examples of the compounds of the formula (I)

| Example No. | R¹ | R² | R³ | X | Y | Melting point (°C.) |
|---|---|---|---|---|---|---|
| 165 | Cl—C₆H₄—CH₂—CH₂—CH(CH₃)— | CH₃ | CH₃ | O | O | 86 |
| 166 | 3,4-(H₃C)₂C₆H₃—O—CH₂—CH(CH₃)— | CH₃ | CH₃ | O | O | 85 |
| 167 | (2,2-dimethylchroman-6-yl)—O—CH₂—CH(CH₃)— | CH₃ | CH₃ | O | O | 90 |
| 168 | 2-methylcyclohexyl (cis) | CH₃ | CH₃ | O | O | 107 |
| 169 | CH₃—O—CH₂—CH(CH₃)— | CH₃ | CH₃ | O | O | 94 |
| 170 | F—C₆H₄—O—CH₂—C(CH₃)₂—CH(CH₃)— | CH₃ | CH₃ | O | O | 122 |
| 171 | 2-methylcyclohexyl (trans) | CH₃ | CH₃ | O | O | 137 |
| 172 | CH₃—O—C₆H₄—CH₂—CH₂— | CH₃ | CH₃ | O | O | 139 |
| 173 | CH₃—O—C₆H₄—O—CH₂—CH(CH₃)— | CH₃ | CH₃ | O | O | 91 |
| 174 | C₆H₅—CH₂—CH₂—CH(CH₃)— | CH₃ | CH₃ | O | O | 59 |

Starting Substances of the Formula (II)

EXAMPLE (II-I)

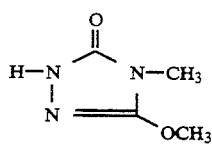

In 100 ml of absolute o-dichlorobenzene, 50.2 g (0.33 mol) of phenyl hydrazinoformate and 36.6 g (0.33 mol, 93%) of trimethyl iminocarbonate are heated to 60° C., and the mixture is stirred for 2 hours, during which process a clear solution forms. This solution is heated to 120° C. in the course of two hours, during which process methanol distils off. A vacuum is applied carefully, during which process more methanol and finally phenol distill off. Upon further distillation, there is formed a fraction which solidifies in the receiver in crystalline form.

After recrystallization from toluene, 7.0 g (0.054 mol, 16% of theory) of 4-methyl-5-methoxy-2,4-dihydro-3H-1,2,4-triazol-3-one are obtained in the form of colourless crystals of melting point 142°–144° C.

Use Examples

In the Use Examples, the following compound (A) is used as Comparison substance:

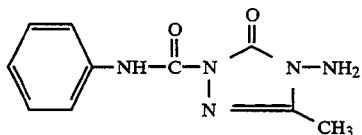

4-amino-5-methyl-2-phenylaminocarbonyl-2,4-dihydro-3H-1,2,4-triazol-3-one (disclosed in EP-A 294,666).

EXAMPLE A

Post,emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1000 l of water/ha. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compounds of Preparation Examples 1 and 2.

EXAMPLE B

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a powerful action against weeds combined with good tolerance by crop plants such as, for example, barley, is shown, for example, by the compound of Preparation Example 2.

It will be appreciated that the instant specification is set forth by way of illustration and not limitation, and that various modifications and changes may be made without departing from the spirit and scope of the present invention.

What is claimed is:

1. A 5-alkoxy-1,2,4-triazol-3-(thi)one of the formula

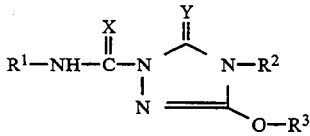

in which $R^1$ represents methyl, ethyl, n- or i-propyl, n-, i-, s- or t-butyl, n-, i-, s- or t-pentyl, n-, i-, s- or t-hexyl, propargyl, n- or i-butinyl, n- or i-pentinyl, or represents straight-chain or branched halogenoalkyl having 1 to 4 carbon atoms and 1 to 4 identical or different halogen atoms, or represents cyanomethyl, cyanoethyl or n- or i-cyanopropyl, or represents cyclopropyl, cyclopropylmethyl, cyclopentyl, cyclopentylmethyl, cyclohexyl or cyclohexylmethyl, each of which is optionally monosubstituted to trisubstituted by identical or different substituents, the substituents in the cyclic and if appropriate in the aliphatic moiety being selected from the group consisting of fluorine, chlorine, bromine, methyl, ethyl, n- or i-propyl, n-, i-, s- or t-butyl, cyano, methanediyl, ethanediyl, butanediyl and butadienediyl, or represents phenyl, benzyl or phenylethyl, each of which is optionally monosubstituted to trisubstituted by identical or different substituents selected from the group consisting of fluorine, chlorine, bromine, methyl, ethyl and trifluoromethyl, or represents in each case straight-chain or branched phenylpropyl, phenylbutyl, phenylpentyl or phenylhexyl, $R^2$ represents methyl, ethyl, n-propyl, i-propyl or cyclopropyl, n-, i-, s- or t-butyl, $R^3$ represents methyl, ethyl, n- or i-propyl, n-, i-, s- or t-butyl, n- or i-pentyl, X represents oxygen and
Y represents oxygen.

2. A compound according to claim 1, wherein such compound is 2-tert.-butylaminocarbonyl-5-methoxy-4-methyl-2,4-dihydro-3H-1,2,4-triazol-3-one of the formula

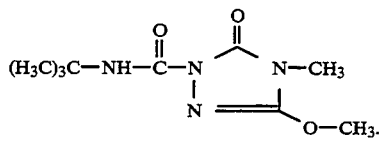

3. A compound according to claim 1, wherein such compound is 2-tert.-chlorobutylaminocarbonyl-5-methoxy-4-methyl-2,4-dihydro-3H-1,2,4-triazol-3-one of the formula

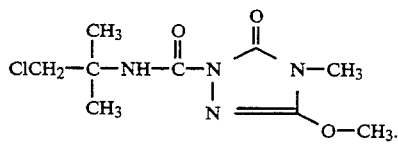

4. A herbicidal composition comprising a herbicidally effective amount of a compound according to claim 1 and a diluent.

5. A method of combating unwanted vegetation which comprises applying to such vegetation or to a locus from which it is desired to exclude such vegetation a herbicidally effective amount of a compound according to claim 1.

6. The method according to claim 5, wherein such compound is 2-tert.-butylaminocarbonyl-5-methoxy-4-methyl-2,4-dihydro-3H-1,2,4-triazol-3-one   2-tert.-chlorobutylaminocarbonyl-5-methoxy-4-methyl-2,4-dihydro-3H-1,2,4-triazol-3-one.

7. A 5-methoxy-1,2,4-triazol-3-one of the formula

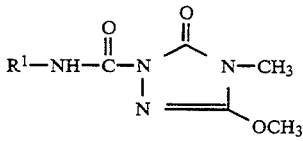

in which $R^1$ is alkyl having up to 6 carbon atoms or cycloalkyl having 3 to 6 carbon atoms, each optionally substituted by phenyl, halophenyl, cycloalkyl having 3 to 8 carbon atoms, methylcycloalkyl having 3 to 8 carbon atoms in the cycloalkyl moiety or alkynyl having 2 to 8 carbon atoms.

* * * * *